United States Patent [19]
Motley et al.

[11] Patent Number: 5,932,196
[45] Date of Patent: Aug. 3, 1999

[54] BUFFERED EMULSION COMPOSITIONS CONTAINING ACTIVES SUBJECT TO ACID OR BASE HYDROLYSIS

[75] Inventors: Curtis Bobby Motley, West Chester, Ohio; Patricia Sue Raleigh, Alexandria, Ky.

[73] Assignee: The Procter & Gamble Company, Cincinnati, Ohio

[21] Appl. No.: 08/334,466

[22] Filed: Nov. 4, 1994

[51] Int. Cl.$^6$ ...................................... A61K 7/48
[52] U.S. Cl. .............. 424/62; 424/401; 514/75; 514/183; 514/210; 514/212; 514/317; 514/331; 514/424; 514/426; 514/408; 514/450; 514/459; 514/460; 514/461; 514/471; 514/472; 514/473; 514/475; 514/646; 514/678; 514/699; 514/706; 514/708; 514/709
[58] Field of Search ............... 424/62, 401; 514/844, 514/937, 75, 183, 210, 212, 317, 331, 424, 426, 408, 450, 459, 460, 461, 471, 472, 473, 475, 646, 678, 699, 706, 708, 709

[56] References Cited

U.S. PATENT DOCUMENTS

| | | | |
|---|---|---|---|
| 4,764,505 | 8/1988 | Fujinuma et al. | 514/35 |
| 4,877,654 | 10/1989 | Wilson | 427/387 |
| 5,037,873 | 8/1991 | Heaton | 524/267 |
| 5,346,693 | 9/1994 | Pilleux et al. | 424/62 |

FOREIGN PATENT DOCUMENTS

| | | |
|---|---|---|
| 0 524 109A1 | 1/1993 | European Pat. Off. . |
| A 2 577 805 | 8/1986 | France . |
| WO 91/02517 | 3/1991 | WIPO . |
| WO 95/23780 | 9/1995 | WIPO . |

OTHER PUBLICATIONS

JP,6192062 Abstract, Patent Abstracts of Japan Oct. 17, 1994, (No. 542, vol. 018, Jul. 12, 1994).
JP,62089608 Abstract, Patent Abstracts of Japan Sep. 25, 1987, (No. 297, vol. 011, Apr. 24, 1987).
JP,63008314 Abstract, Patent Abstracts of Japan Jun. 15, 1988, (No. 209, vol. 012, Jan. 14, 1988).
Schick and Fowkes, *Nonionic Surfactants, Surfactant Science Series*, "Emulsification", (ed. M. J. Schick), vol. 2, pp. 607–613, New York, NY (1966).
Perin and Dempsey, *Buffers for pH and Metal Ion Control*, "Appendix II and III", pp. 139–157, published by Chapman and Hall Ltd. (1974).
*Remington's Pharmaceutical Science*, "Course Dispersions", (ed. J. E. Hoover) 15th Edition, pp. 335–337, Easton, PA, (1975).
Wilkinson and Moore, *Harry's Cosmeticology*, "Emulsions", 7th Edition, pp. 737–739, Great Britain (1982).
*McCutcheon's vol. 1, Emulsifiers & Detergents*, "HLB Index", pp. 237–239, Glen Rock, NJ (1994).

*Primary Examiner*—Jyothsna Venkat
*Attorney, Agent, or Firm*—John M. Howell; Loretta J. Henderson; George W. Allen

[57] ABSTRACT

The present invention are for emulsion compositions and the process for making such compositions containing biological and cosmetic actives subject to hydrolysis of actives during processing and storage of the emulsion composition. Buffers are incorporated into emulsion at a point wherein the acidic and basic conditions created during processing have little effect on compositions.

14 Claims, No Drawings

BUFFERED EMULSION COMPOSITIONS CONTAINING ACTIVES SUBJECT TO ACID OR BASE HYDROLYSIS

TECHNICAL FIELD

The present invention relates to the field of improved emulsion products containing active compounds subject to hydrolysis wherein hydrolysis of said actives is eliminated.

BACKGROUND OF THE INVENTION

Emulsion compositions containing active compounds are known in the art. For example, WO 91/02517 published Mar. 7, 1991 discloses an oil-in-water emulsion of a drug which is poorly soluble in water. Said drug is dissolved in a solution of high or low pH to facilitate dissolution. Said acidic or basic drug-containing solution is added to a preformed emulsion which itself contains an acid, base, or buffer to neutralize the emulsion once the active solution is added.

Emulsion products containing actives subject to hydrolysis may be negatively effected during processing or storage from acidic or basic conditions created during processing of such products. Aside from the use of acids and bases to make the product, the acidic or basic character of the emulsion products is also attributable to the raw materials comprising the emulsion. For example the final emulsion product can be more or less acidic depending on the source of the water used. Furthermore, acidic or basic conditions can be created when the final emulsion product is pH balanced with an acid or base. Therefore, there is a need for the development of emulsion compositions and processes for making said emulsion compositions which are uneffected by the acidic or basic conditions found during production and even storage of such products.

It is therefore an objective in the present invention to create emulsion compositions comprising active compounds subject to acid or base hydrolysis having improved efficacy and product aesthetics. It is a further objective of the present invention to provide a process for making said emulsion compositions. Another object of the present invention is to make skin care products used in regimens of men and women, including products containing skin lightening actives to lighten basal skin tone and hyperpigmented lesions.

SUMMARY OF THE INVENTION

The present invention relates to emulsion compositions comprising:
a) an aqueous phase containing a buffer having a pH from about 3 to about 12;
b) an oil phase;
c) an active compound; and
d) an emulsifier;
wherein said emulsion composition contains a sufficient level of said buffer to eliminate hydrolysis of said actives during the production and storage of the said emulsion composition, particularly emulsion compositions containing skin lightening actives. The present invention further relates to the process for making said emulsion compositions and methods of use for said compositions made by this process.

DETAILED DESCRIPTION OF THE INVENTION

Emulsion compositions generally comprise two phases which are incompatible; i.e. do not readily mix or remain homogeneous after mixing. In order to form an emulsion of non-immisible phases such as oil and water, one phase is sufficiently dispersed into the other phase whereby the individual droplets or particles of the dispersed phase resist the tendency to coalesce whereby the phases separate. Critical to achieving this is the presence of an agent or emulsifier to provide an interface which makes said phases compatible with each other. A more detailed discussion regarding the dynamics of these systems in cosmetic product manufacturing can be found in Wilkinson and Moore, *Harry's Cosmeticology*, 7th Ed. 1982, pp. 729–756; incorporated herein by reference.

A. Aqueous Phase

The aqueous phase of the emulsion comprises the water, including the water comprising the buffer solution, and other water-soluble components comprising said emulsion.

1. Buffer

In the present invention the buffer is used at a level sufficient to eliminate hydrolysis of said actives, particularly skin lightening actives incorporated into the emulsion compositions of the present invention. It is herein understood that "eliminated" means that no more than 25% of the active is hydrolyzed.

Buffers useful in the present invention comprise those disclosed in Perin and Dempsey, *Buffers for pH and Metal Ion Control*, 1994 (published by Chatman and Hall) New York, N.Y. The buffers disclosed for use herein may be purchased or made from mixtures of weak acids and salts of strong bases, and mixtures of weak bases and salts of strong acids. In the present invention, the buffers are preferably selected from the group consisting of triethanolamine hydrochloride and sodium hydroxide, sodium borate and hydrochloric acid, boric acid and sodium hydroxide, sodium borate and sodium hydroxide, phosphate buffer, potassium phosphate and sodium hydroxide, glycine and sodium hydroxide, diethanolamine and hydrochloric acid, tris (hydroxyl methyl) aminomethane and hydrochloric acid, sodium carbonate and sodium hydroxide, sodium phosphate and sodium hydroxide, citric acid and sodium phosphate, and mixtures thereof having a pH from about 3 to about 12. Preferred buffers in the present invention are selected from the group consisting of triethanolamine hydrochloride and sodium hydroxide, sodium borate and hydrochloric acid, phosphate buffer, potassium phosphate and sodium hydroxide, glycine and sodium hydroxide, diethanolamine and hydrochloric acid, tris (hydroxyl methyl) aminomethane and hydrochloric acid, citric acid and sodium phosphate, and mixtures thereof having a pH of from about 7.0 to 10. Most preferred buffers in the present invention are selected from the group consisting of triethanolamine hydrochloride and sodium hydroxide, phosphate buffer, potassium phosphate and sodium hydroxide, and mixtures thereof having a pH of from about 7.0 to about 8.8.

The buffers are preferably incorporated into the aqueous phase prior to combining the oil phase and aqueous phase. Additional buffer may be added at any point throughout the production of said emulsion. The actual levels of said buffers depend on the degree to which acidic and/or basic conditions are created during formation of the emulsion composition, as disclosed below, or upon pH balancing the emulsion. The concentration of the buffers used in the present invention is from about 0.05 M to about 2M, preferably from about 0.1M to 1M, and most preferable from about 0.15M to about 0.75M.

2. Water-Soluble Ingredients

The aqueous phase also compries water-soluble ingredients used to make the final emulsion product. The water-soluble ingredients useful in the present invention include alcohols, glycols, preservatives, skin conditioning components and mixtures thereof.

B. Oil Phase

The oil phase of the present invention comprises lipophilic materials capable of solubilizing said biological and cosmetic active compounds, particularly skin lightening actives. The oil phase comprises from about 5% to about 25%, preferably from about 7% to about 15%, and most preferably from about 7% to about 12% of the emulsion composition.

The oil phase comprises lipophilic materials typically liquids at room temperature selected from the group consisting of oils, fats, fatty acid esters, fatty acid ethers have a solubility parameter from about 2 to about 20, preferably from about 4 to about 17, and most preferably from about 5 to about 16 as measured using the method disclosed by C. D. Vaughan, "Solubility Effects in Product,Package, Penetration and Preservation", 103 Cosmetics and Toiletries, p. 47–69, October, 1988; and C. D. Vaughan, "Using Solubility Parameters in Cosmetic Formulation", 36 J. Soc. Cosmetic Chemists, 319–333, September/October, 1985; both incorporated herein by reference.

Said lipophilic materials are selected from the group consisting of non-polar volatile oils, non-polar non-volatile oils, polar volatile oils, polar non-volatile oils, and mixtures thereof; preferably non-polar volatile oils, polar non-volatile oils and mixtures thereof The term "non-polar" typically means that the emollient has a solubility parameter below about 16.

Non-polar volatile oils include silicone oils, hydrocarbons, and mixtures thereof Such non-polar volatile oils are disclosed, for example, in Cosmetics, Science, and Technology, Vol. 1, 27–104 edited by Balsam and Sagarin, 1972, incorporated herein by reference. The non-polar, volatile oils useful in the present invention may be saturated or unsaturated, straight or branched chained, aliphatic or aromatic. Preferred non-polar volatile hydrocarbons include isodecane (such as ERMETHYL-99A®, available from Presperse Inc.) and the $C_7$–$C_8$ through $C_{12}$–$C_{15}$ isoparaffins (such as the SOPAR® Series available from Exxon Chemicals).

Non-polar volatile oils include silicone oils. Said oils are highly preferred because they provide the composition with highly desirable aesthetics. Non-polar volatile liquid silicone oils are disclosed in U.S. Pat. 4,781,917 issued to Luebbe et al., on Nov. 1, 1988; and in Todd et al., "Volatile Silicone Fluids for Cosmetics", Cosmetics and Toiletries, V. 91, pp. 27–32 (1976); both incorporated herein by reference. Particularly preferred volatile silicone oils include cyclic volatile silicones corresponding to the formula:

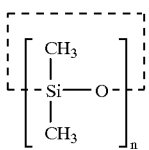

wherein n is from about 3 to about 7; and linear volatile silicones corresponding to the formula:

wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of non-polar volatile silicone oils include cyclomethicones of varying viscosities, e.g., DOW CORNING 200®, DOW CORNING 244®, DOW CORNING 245®, DOW CORNING 344®, and DOW CORNING 345®, (commercially available from Dow Corning Corp.); SF-1204® and SF-1202® SILICONE FLUIDS (commercially available from G.E. Silicones), GE 7207® and 71584® (commercially available from General Electric Co.); and SWS-03314® (commercially available from SWS Silicones Corp.).

The phrase "relatively polar" as used herein means more polar than another material in terms of solubility parameter; i.e., the higher the solubility parameter the more polar the liquid. The non-volatile solvent is "relatively polar" as compared to the non-polar volatile oil discussed above. Therefore, the non-volatile solvent is more polar (i.e., has a higher solubility parameter) than at least one of the non-polar volatile oils.

Relatively polar non-volatile oils useful in the present invention are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989; all incorporated herein by reference. The relatively polar non-volatile oils useful in the subject invention may be either saturated or unsaturated, have an aliphatic character and be straight or branched chained or contain aliphatic rings or aromatic rings. Said polar non-volatile oils useful in the subject invention preferably include silicone oils; hydrocarbon oils; fatty alcohols; fatty acids; esters of mono and dibasic carboxylic acids with mono and polyhydric alcohols; polyoxyethylenes; polyoxypropylenes; mixtures of polyoxyethylene and polyoxypropylene ethers of fatty alcohols; and mixtures thereof.

More preferably, the relatively polar non-volatile oils include fatty alcohols having from about 12–26 carbon atoms; fatty acids having from about 12–26 carbon atoms; esters of monobasic carboxylic acids and alcohols having from about 14–30 carbon atoms; esters of dibasic carboxylic acids and alcohols having from about 10–30 carbon atoms; esters of polyhydric alcohols and carboxylic acids having from about 5–26 carbon atoms; ethoxylated, propoxylated, and mixtures of ethoxylated and propoxylated ethers of fatty alcohols with from about 12–26 carbon atoms and a degree of ethoxylation and propoxylation of below about 50; and mixtures thereof.

More preferred relatively polar non-volatile oils include propoxylated ethers of $C_{14}$–$C_{18}$ fatty alcohols having a degree of propoxylation below about 50, esters of $C_2$–$C_8$ alcohols and $C_{12}$–$C_{26}$ carboxylic acids (e.g. ethyl myristate, isopropyl palmitate), esters of $C_{12}$–$C_{26}$ alcohols and benzoic acid (e.g. Finsolv TN supplied by Finetex), benzyl alcohol, $C_2$–$C_8$ alcohols and adipic, sebacic, and phthalic acids (e.g., diisopropyl sebacate, diisopropyl adipate, di-n-butyl phthalate), polyhydric alcohol esters of $C_6$–$C_{26}$ carboxylic acids (e.g., propylene glycol dicaprate/dicaprylate, propylene glycol isostearate); and mixtures thereof.

Even more preferred relatively polar non-volatile oils include branched-chain aliphatic fatty alcohols having from about 12–26 carbon atoms, such as isocetyl alcohol, stearyl alcohol, cetyl alcohol, octyldodecanol and undecylpentadecanol. Such preferred aliphatic fatty alcohols are particularly useful in combination with the volatile liquid silicone oils discussed herein to adjust the average solubility of the liquid base material.

In addition to the liquids discussed above, the lipophilic materials may optionally include non-volatile, non-polar emollients which tend to improve product cosmetics. Typical non-volatile, non-polar emollients are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989; all incorporated herein by reference. The non-volatile silicone oils useful in the present invention are essentially non-volatile polysiloxanes, paraffinic hydrocarbon oils, and mixtures thereof The polysiloxanes useful in the subject invention include polyalkylsiloxanes, polyarylsiloxanes, polyalkylarylsiloxanes, polyethersiloxane copolymers, and mixtures thereof Examples of these include polydimethyl siloxanes having viscosities of from about 5 to about 100,000 centistokes at 25° C.

Among the preferred non-volatile silicone emollients useful in the subject compositions are the polydimethyl siloxanes having viscosities from about 2 to about 400 centistokes at 25° C. Such polyalkylsiloxanes include the Viscasile series (sold by General Electric Company) and the Dow Corning 200® series (sold by Dow Corning Corp.). Polyalkylarylsiloxanes include polymethylphenyl siloxanes having viscosities of from about 15 to about 65 centistokes at 25° C. These are available, for example, as SF 1075 METHYL-PHENYL FLUID® (sold by General Electric Company) and 556 COSMETIC GRADE FLUID® (sold by Dow Corning Corp.). Useful poly-ethersiloxane copolymers include, for example, a polyoxyalkylene ether copolymer having a viscosity of about 1200 to 1500 centistokes at 25° C. Such a fluid is available as SF1066® organosilicone surfactant (sold by General Electric Company). Polysiloxane ethylene glycol ether copolymers are preferred copolymers for use in the subject compositions.

Non-volatile paraffinic hydrocarbon oils useful in the subject invention include mineral oils and certain branched-chain hydrocarbons. Examples of these fluids are disclosed in U.S. Pat. No. 5,019,375 issued to Tanner et al. on May 28, 1991, incorporated herein by reference. Preferred mineral oils have the following properties: viscosity from about 5 centistokes to about 70 centistokes at 40° C.; density between about 0.82 and 0.89 g/cm³ at 25° C.; flash point between about 138° C. and about 216° C.; and carbon chain length between about 14 and about 40 carbon atoms.

Preferred branched chain hydrocarbon oils have the following properties: density between about 0.79 and about 0.89 g/cm³ at 20° C.; boiling point greater than about 250° C.; and flash point between about 110° C. and about 200° C.

Particularly preferred branched-chain hydrocarbons include PERMETHYL 103A®, which contains an average of about 24 carbon atoms; PERMETHYL 104A®, which contains an average of about 68 carbon atoms; PERMETHYL 102A®, which contains an average of about 20 carbon atoms; all of which may be purchased from Permethyl Corporation; and ETHYLFLO 364® which contains a mixture of 30 carbon atoms and 40 carbon atoms and may be purchased from Ethyl Corp.

It is important that the liquid material be of a type, and used at a level sufficient to solubilize the active ingredients. Furthermore, the liquid base materials are typically selected to provide aesthetic benefits, such as emolliency, low tack and/or minimized visible residue, without significant interference with the effectiveness of the active component. The particular liquid base material should be safe for application to human skin.

C. Active Compounds

Active compounds of the present invention include biological and cosmetic actives subject to partial or full hydrolysis in the presence of acidic or basic conditions. Since said hydrolysis typically has a deleterious effect on the aesthetics and the efficacy of the compositions, it is preferred that said hydrolysis be eliminated.

Skin care emulsion products are included in the present invention. These products are known to address conditions which result in defective or missing tyrosinase, an enzyme involved in the formation of melanin lead to a loss of pigmentation, e.g. albinism. See King, R. A. And C. G. Summers, *Dermatologic Clinics*, Vol. 6 pp. 217–227 (1988). Tyrosinase is present within the melanosomes in epidermal melanocytes and catalyzes the committed step in the formation of melanin from tyrosine. See Goldsmith, L. A., *Physiology, Biochemistry, and Molecular Biology of the Skin*, Oxford University Press, pp. 873–903 (N.Y. 1991). Tyrosinase catalyzes the hydroxylation of tyrosine and the oxidation of DOPA to DOPA quinone:

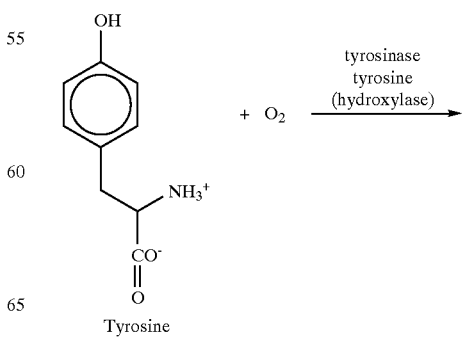
Tyrosine

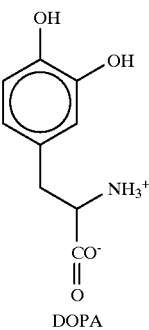

DOPA

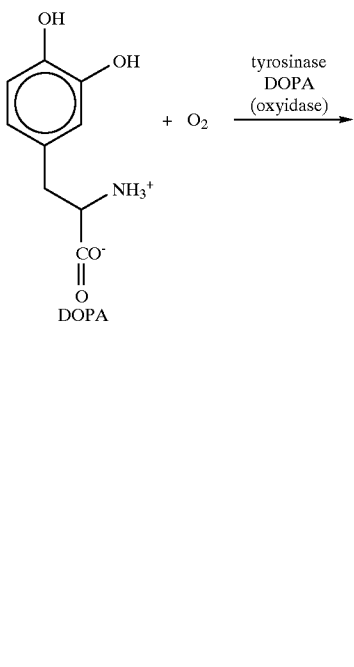

DOPA quinone

Binding of an inhibitor to the active site of tyrosinase results in decreased melanin formation. See generally Prota, G. *Melanins and Melanogenesis* Academic Press, Inc., (San Diego 1992). There currently are tyrosinase inhibitors in products in the market place for lightening skin. These actives including hydroquinone, kojic acid, and arbutin. In addition to these actives is the recently discovered deoxyarbutin as disclosed in co-pending U.S. patent application Ser. No. 08/206,573, filed Mar. 3, 1994; incorporated herein by reference.

Deoxyarbutin corresponds to the formulas

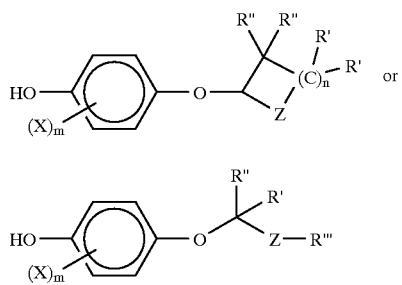

In the above structures each X is, independently, selected from the group consisting of halogen, alkyl, aryl, OR, OCOR, COR, CONR$_2$, COOR, CN, SR, and NR$_2$; each X is preferably independently selected from the group consisting of halogen, alkyl, haloalkyl, arylalkyl, OR and OCOR; more preferably from the group consisting of F, Cl, Br, methyl, OH, OCH$_3$ and OCOCH$_3$.

In the above structures, each R is, independently, selected from the group consisting of hydrogen, alkyl, and aryl; preferably hydrogen or alkyl; most preferably hydrogen.

In the above structures, m is an integer from 0 to 4; preferably 0 to 2; more preferably 0 or 1, most preferably 0.

In the above structures, each R" is, independently, selected from the group consisting of hydrogen, halogen, alkyl, aryl, COR, CONR$_2$, COOR, CN, SR, and NR$_2$; preferably from the group consisting of hydrogen, halogen, haloalkyl, arylalkyl, and alkyl; more preferably from the group consisting of H, F, Cl, Br and methyl; most preferably H.

In the above structures, each R' is, independently, selected from the group consisting of hydrogen, halogen, alkyl, aryl, OR, OCOR, COR, CONR$_2$, COOR, CN, SR, and NR$_2$; preferably from the group consisting of hydrogen, halogen, alkyl, haloalkyl, arylalkyl, OR and OCOR; more preferably from the group consisting of H, F, Cl, Br, methyl, OH, OCH$_3$ and OCOCH$_3$; most preferably H.

In the above structures, n is an integer from 1 to 4; preferably 2 or 3; more preferably 3.

In the above structures, Z is selected from the group consisting of O, NR, S, SO, SO$_2$; and PO$_2$; more preferably O.

In the above structures, R'" is alkyl; more preferably methyl, CF$_3$ or CH$_2$CH$_2$OCH$_3$.

As used in the above structures, "alkyl" means carbon-containing chains which may be straight, branched or cyclic; substituted or unsubstituted; saturated, monounsaturated (i.e. one double or triple bond in the carbon chain), or polyunsaturated (i.e. two or more double bonds in the carbon chain, two or more triple bonds in the carbon chain, one or more double and one or more triple bonds in the carbon chain). Unless otherwise indicated, alkyl are preferably as follows. Preferred alkyl are straight or branched chain, more preferably straight chain. Preferred alkyl are mono, di-, or tri- substituted, or unsubstituted, most preferably unsubstituted. Preferred alkyl are saturated or monounsaturated and, if so, preferably with a double bond; more preferably alkyl are saturated. Preferred alkyl are C$_1$–C$_{10}$, more preferably C$_1$–C$_4$, also more preferably methyl, ethyl and t-butyl, more preferably still methyl and ethyl, most preferably methyl.

Preferred alkyl substituents include halogen, aryl, amino, hydroxy, alkoxy, cyano, nitro and trifluoromethyl. More preferred alkyl substituents are halogen and aryl.

As used in the above structures, "halogen" means F, Cl, Br, and I. Preferred halogens are F, Cl, and Br, more preferably F and Cl, most preferably F.

As used in the above structures, "aryl" means aromatic rings which may be unsubstituted or substituted. Preferred aryl are phenyl or naphthyl, especially phenyl. Preferred aryl are mono-, di-, tri-substituted or unsubstituted; more preferred aryl are monosubstituted or unsubstituted, especially unsubstituted. Preferred aryl substituents include alkyl, halogen, amino, hydroxy, alkoxy, cyano, nitro and trifluoromethyl. More preferred aryl substituents are alkyl and halogen. The most preferred aryl is phenyl.

Pharmaceutically-acceptable salts of the above compounds are also suitable.

As used in regard to the above structures, "pharmaceutically-acceptable salts" include Na$^+$, K$^+$, Ca$^{++}$, Mg$^{++}$, Al$_2$(OH)$_5{}^+$, NH$_4{}^+$, (HOCH$_2$CH$_2$)$_3$NH$^+$, (CH$_2$CH$_2$)$_3$NH$^+$, (CH$_3$CH$_2$)$_4$N$^+$, C$_{12}$H$_{25}$(CH$_3$)$_3$N$^+$ and C$_{12}$H$_{25}$ ($C_5H_4N)_3N^+$. Preferred salts include $Na^+$, $K^+$, $NH_4^+$, and $(HOCH_2CH_2)_3NH^+$. More preferred salts include $Na^+$ and $NH_4^+$.

As used in regard to the above structures, "pharmaceutically-acceptable salts" means that the salts are suitable for use in contact with the tissues of humans and lower animals without undue toxicity, incompatibility, instability, irritation, allergic response, and the like, commensurate with a reasonable benefit/risk ratio.

Preferred compounds of the subject invention include.

4-[(tetrahydro-2H-pyran-2-yl)oxy] phenol ("THPOP") which has the structure:

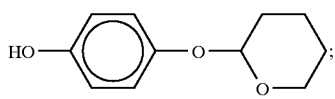

4-[(tetrohydro-2H-pyran-2-yl)oxy]-2-chlorophenol which has the structure:

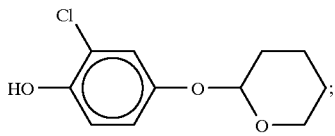

4-[(tetrahydro-2H-pyran-2-yl)oxy]-2-fluorophenol which has the structure:

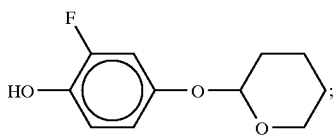

4-[(tetrahydrofuran-2-yl)oxy]phenol which has the structure:

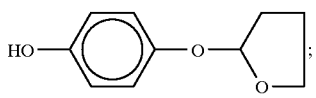

4-[(methoxymethyl)oxy]phenol which has the structure:

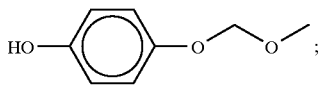

4-[(2-methoxyethoxymethyl)oxy]phenol which has the structure:

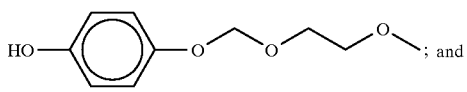

and

4-[(tetrahydro2H-pyran-2-yl)oxy]-2,3,5,6-tetrafluorophenol which has the structure:

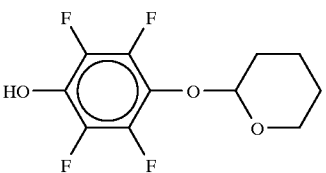

The most preferred compound preferred compound of the subject invention is THPOP.

Emulsion compositions of the present invention contain skin lightening actives at levels from about 0.1% to about 10%, preferably from about 0.75% to about 6%, and most preferably from about 1.0% to about 3% of the emulsion composition.

D. Emulsifier

Emulsion compositions of the present invention include "water-in-oil" and "oil-in-water" emulsions. As discussed in the reference above, there are many factors which determine whether the water or the oil end up the dispersed or continuous phase. However, the single most important factor is what the hydrophilic-lipophilic balance value (herein referred to as HLB) of the emulsifier; Wilkinson and Moore, *Harry's Cosmeticology*, 7th Ed. 1982, p. 738. For example Schick and Fowkes, Surfactant Science Series, Vol. 2, *Solvent Properties of Surfactant Solutions*, p 607. Schick and Fowkes discloses that HLB values of surfacant emulsifiers for making water-in-oil emulsions is from 3–6 whereas for making oil-in-water emulsions is from 8–15. Since the emulsions of the present invention includes both types of emulsion mentioned above the emulsifiers selected for use in the present invention are those having an HLB from 3 to about 15. Said emulsifiers include those disclosed in the C.T.F.A. Cosmetic Ingredient Handbook, 1992, pp.587–592; and Remington's Pharmaceutical Sciences, 15th Ed. 1975, pp 335–337; both incorporated herein by reference. Since "oil-in-water" are preferred, the preferred emulsifier of the present invention has an HLB value from about 3 to about 6. Said emulsifiers are selected from those known in the art and mixtures thereof including those in McCutcheon's Volume 1, *Emulsifiers & Detergents*. 1994, North American Edition, pp. 236–239; herein incorporated by reference. Most preferred are those selected from the group consisting of cetyl alcohol, stearyl alcohol, steareth-21, steareth-2 and mixtures thereof.

Process for Making Emulsion Compositions of the Present Invention

The active compounds in the compositions of the present invention are protected from hydrolysis due to the acidic or basic conditions that are created during production of said emulsion. The emulsion compositions of the present invention including both water-in-oil and oil-in-water emulsions are manufactured using the process described herein below.

Prepare the aqueous phase by adding water into steam-jacketed vessel equiped with mixing. While mixing add the water-soluble ingredients of the emulsion composition into said water. Heat until the mixture is about 80° C., wherein this temperature is maintained for about 30 minutes. Add the buffer to said aqueous phase in a sufficient amount to bring the pH of said aqueous phase to between about 3 and about 12, preferably from about 7 to about 12.

Prepare the oil phase by adding the lipophilic materials into a second steam-jacketed vessel equiped with mixing. Bring the temperature of the solubilizing lipophilic material to about 80° C., add the active compound, and continue to mix until homogeneous.

Add the emulsifier to either the oil phase or the aqueous phase and combine the phases with heat and mixing to form a homogeneous mixture at about 80° C. Insert a homogenizer set at about 5000 rpm, such as an Ultra Tumax T-50, in the vessel wherein said mixture is homogenized for about 3 minutes. After discontinuing homogenization continue to mix the emulsion composition at medium speed until said emulsion cools to about 60° C.

Add the remaining ingredients, such as the preservatives, to a third vessel equipped with mixing bringing the mixture's temperature to about 55° C. Mix until these ingredients are homogeneous, then mix them into said emulsion until a homogeneous emulsion forms. If necessary, add additional buffer until the emulsion has a pH from about 3 to about 12, preferably from about 7 to about 12.

A modification to the process disclosed above involves the addition of the acid and base salts comprising the buffer to the water of said aqueous phase. A separate or additional modification to the process above involves adding the buffer after the emulsion is formed and homogenized.

| INGREDIENTS | EXAMPLES % W/W |
|---|---|
| Aqueous Phase | |
| 0.2M TEA Hydrochloride[1] | 49.11 |
| 0.2M Sodium Hydroxide[2] | 32.74 |
| Butylene Glycol | 1.50 |
| Disodium EDTA | 0.05 |
| Methyl Paraben | 0.25 |
| Sodium Metabisulfite | 0.05 |
| Magnesium Ascorbyl Phospate[3] | 0.10 |
| Oil Phase | |
| PPG-14 Butyl Ether[4] | 5.00 |
| Active[5] | 3.00 |
| Ascorbyl Palmitate | 0.10 |
| Cetyl Alcohol | 3.00 |
| Stearyl Alcohol | 1.50 |
| Steareth-21[6] | 2.00 |
| Steareth-2[7] | 1.00 |
| Propylparaben | 0.10 |
| Benzyl Alcohol | 0.50 |
| Total | 100.00 |

[1]Acid salt dissolved in water to create the buffer
[2]Base salt dissolved in water to create the buffer
[3]Nikkol VC-PMG available from Nikko Chemical Company, Ltd.; Japan
[4]Fluid AP available from Union Carbide
[5]Deoxyarbutin
[6]Brij 721 available from ICI Americas
[7]Brij 72 available from ICI Americas

| | EXAMPLES % W/W |
|---|---|
| Aqueous Phase | |
| Water | 75.25 |
| Magnesium Ascorbyl Phospate[1] | 0.10 |
| 1N Hydrochloric Acid | 2.80 |
| Triethanolamine | 1.40 |
| Oil Phase | |
| PPG-14 Butyl Ether[2] | 7.50 |
| Active[3] | 3.00 |
| Ascorbyl Palmitate | 0.10 |
| Cetyl Alcohol | 3.00 |
| Stearyl Alcohol | 1.50 |
| Steareth-2[4] | 1.00 |
| Steareth-21[5] | 2.00 |
| Cyclomethicone[6] | 1.00 |
| Butylene Glycol | 1.00 |
| Disodium EDTA | 0.05 |
| Glydant Plus[7] | 0.30 |
| Total | 100.00 |

[1]Nikkol VC-PMG available from Nikko Chemical Company, Ltd.; Japan
[2]Fluid AP available from Union Carbide
[3]Deoxyarbutin
[4]Brij 72 available from ICI Americas
[5]Brij 721 available from ICI Americas
[6]DC 344 Fluid available from Dow Corning Corporation
[7]DMDM Hydantoin and Lodopropynyl Butylcarbamate available from Lonza, Inc.

What is claimed is:

1. An emulsion composition comprising:
   a) an aqueous phase containing a buffer having a pH from about 3 to about 12;
   b) an oil phase;
   c) an active corresponding to the formula:

$$HO-\underset{(X)_m}{\bigcirc}-O-\underset{Z}{\overset{R''\ R''}{\underset{|\ \ |}{C}}}(C)_n^{R'}-R'\ \ \text{or}$$

$$HO-\underset{(X)_m}{\bigcirc}-O-\underset{}{\overset{R''}{\underset{|}{C}}}-Z-R'''$$

wherein:
   (i) each X is, independently, selected from the group consisting of halogen, $C_1$–$C_{10}$ alkyl, substituted $C_1$–$C_{10}$alkyl, substituted or unsubstituted phenyl, substituted or unsubstituted naphthyl, OR, OCOR, COR, $CONR_2$, COOR, CN, SR, and $NR_2$;
   (ii) each R is, independently, selected from the group consisting of hydrogen, $C_1$–$C_{10}$ alkyl, substituted $C_1$–$C_{10}$ alkyl, substituted or unsubstituted phenyl, and substituted or unsubstituted naphthyl;
   (iii) m is an integer from 0 to 4;
   (iv) each R" is, independently, selected from the group consisting of hydrogen, halogen, $C_1$–$C_{10}$ alkyl, substituted $C_1$–$C_{10}$ alkyl, substituted or unsubstituted phenyl, substituted or unsubstituted naphthyl, COR, $CONR_2$, COOR, CN, SR, and $NR_2$;
   (v) each R' is independently selected from the group consisting of hydrogen, halogen, $C_1$–$C_{10}$ alkyl, substituted $C_1$–$C_{10}$ alkyl, substituted or unsubstituted phenyl, substituted or unsubstituted naphthyl, OR, OCOR, COR, $CONR_2$, COOR, CN, SR, and $NR_2$;
   (vi) n is an integer from 1 to 4;
   (vii) Z is selected from the group consisting of O, NR, S. SO, $SO_2$, and $PO_2$; and
   (viii) R''' is $C_1$–$C_{10}$ alkyl or substituted $C_1$–$C_{10}$ alkyl;
   or pharmaceutically-acceptable salts thereof;
   wherein the substituted $C_1$–$C_{10}$ alkyl, the substituents are selected from the group consisting of halogen, phenyl, naphthyl, amino hydroxy, alkoxy, cyano, nitro and trifluoromethyl; and wherein the substituted phenyl and naphthyl, the substituents are selected from the group consisting of $C_1$–$C_{10}$alkyl, halogen, amino, hydroxy, alkoxy, cyano, nitro and trifluoromethyl; and
   d) an emulsifier;
   wherein the emulsion composition contains a sufficient level of the buffer to eliminate hydrolysis of the active during the production and storage of the emulsion composition.

2. The composition according to claim 1 wherein the active is used at a level from about 0.1% to about 10% of the composition.

3. The composition according to claim 1 wherein the buffer is selected from the group consisting of triethanolamine, hydrochloride and sodium hydroxide; sodium borate and hydrochloric acid; boric acid and sodium hydroxide; sodium borate and sodium hydroxide; phosphate buffer; potassium phosphate and sodium hydroxide; glycine and sodium hydroxide; diethanolamine and hydrochloric acid; tris (hydroxyl methyl) aminomethane and hydrochloric acid; sodium carbonate and sodium hydroxide; sodium phosphate and sodium hydroxide; citric acid and sodium phosphate and mixtures thereof having a pH from about 3 to about 12.

4. The composition according to claim 3 wherein the buffer is selected from the group consisting of triethanolamine hydrochloride and sodium hydroxide; phosphate buffer; potassium phosphate and sodium hydroxide; and mixtures thereof having a pH of from about 7.0 to about 8.8.

5. The composition according to claim 4 wherein concentration of the buffer is from about 0.05M to about 2.0M.

6. The composition according to claim 1 wherein the oil phase comprises from about 5% to about 25%, based on the weight of the emulsion composition, lipophilic materials selected from the group consisting of oils, fats, fatty acid esters, and fatty acid ethers having a solubility parameter of from about 2 to about 20.

7. The composition according to claim 6 wherein the oil phase comprises from about 7% to about 15%, based on the weight of the emulsion composition, of the lipophilic materials.

8. The composition according to claim 1 wherein the emulsifier has an HLB from about 3 to about 15.

9. The composition according to claim 8 wherein said emulsifiers are selected from the group consisting of cetyl alcohol, stearyl alcohol, steareth-21, steareth-2 and mixtures thereof.

10. The composition according to claim 1 wherein the deoxyarbutin is used at a level from about 1 0% to about 3.0% of the composition.

11. The composition according to claim 1 wherein the concentration of the buffer is from about 0.15M to about 0.75M.

12. The composition according to claim 1 wherein the emulsifier has an HLB value from about 3 to about 6.

13. The composition of claim 1 wherein the oil phase comprises a lipophilic material and the active compound is soluble in the lipophilic material.

14. The composition of claim 1 wherein the substituted $C_1$–$C_{10}$ alkyl is $CH_2CH_2OCH_3$.

* * * * *

UNITED STATES PATENT AND TRADEMARK OFFICE
CERTIFICATE OF CORRECTION

PATENT NO. : 5,932,196
DATED : August 3, 1999
INVENTOR(S) : Motley et al.

It is certified that error appears in the above-identified patent and that said Letters Patent is hereby corrected as shown below:

In Col. 3, line 40, "thereof" should read --thereof.--.

In Col. 5, line 30, "thereof" should read --thereof.--.
In Col. 5, line 32, "thereof" should read --thereof.--.
In Col. 5, line 40, "Viscasile" should read --Viscasil--.
In Col. 7, line 43, "Melanogensis" should read --Melanogensis,--.
In Col. 10, line 42, "Detergents." should read --Detergents,--.
In Col. 12, line 53, "S." should read --S,--.

Signed and Sealed this

Sixth Day of March, 2001

Attest:

NICHOLAS P. GODICI

Attesting Officer

Acting Director of the United States Patent and Trademark Office